United States Patent
Lee (10) Patent No.: US 7,879,069 B2
(45) Date of Patent: Feb. 1, 2011

(54) ANTI-POOLING VEST FOR PATIENTS UNDERGOING HEMODIALYSIS AND IN CRITICAL CARE

(75) Inventor: Jen-shih Lee, Rancho Santa Fe, CA (US)

(73) Assignee: Global Monitors, Inc., Rancho Sante Fe, CA (US)

( * ) Notice: Subject to any disclaimer, the term of this patent is extended or adjusted under 35 U.S.C. 154(b) by 121 days.

(21) Appl. No.: 12/062,944

(22) Filed: Apr. 4, 2008

(65) Prior Publication Data

US 2009/0112129 A1   Apr. 30, 2009

Related U.S. Application Data (60) Provisional application No. 61/000,436, filed on Oct. 26, 2007.

(51) Int. Cl.
  *A61B 17/00*  (2006.01)
  *A61H 7/00*   (2006.01)
  *A61H 19/00*  (2006.01)
(52) U.S. Cl. .................. 606/201; 606/202; 601/151
(58) Field of Classification Search ............ 601/23, 601/41–44, 148–153; 606/201–203
  See application file for complete search history.

(56) References Cited

U.S. PATENT DOCUMENTS

| | | | | | |
|---|---|---|---|---|---|
| 2,588,192 | A | * | 3/1952 | Akerman et al. | 601/44 |
| 3,683,655 | A | * | 8/1972 | White et al. | 601/44 |
| 3,920,008 | A | * | 11/1975 | Lehman | 128/96.1 |
| 3,933,150 | A | * | 1/1976 | Kaplan et al. | 601/151 |
| 4,135,503 | A | * | 1/1979 | Romano | 602/13 |
| 4,455,685 | A | * | 6/1984 | Steffler et al. | 2/2.11 |
| 4,534,338 | A | | 8/1985 | Crosbie et al. | |
| 4,718,891 | A | * | 1/1988 | Lipps | 604/31 |
| 4,840,167 | A | * | 6/1989 | Olsson et al. | 601/41 |
| 4,925,133 | A | | 5/1990 | Wurst et al. | |
| 4,926,873 | A | | 5/1990 | Frankenreiter | |

(Continued)

OTHER PUBLICATIONS

Maggiore et al., Thermal balance and dialysis hypotension. Int J Artif Organs. Sep. 1995; 18(9):518-525. See abstract.*

(Continued)

*Primary Examiner*—Steven O Douglas
*Assistant Examiner*—Kristen C Matter
(74) *Attorney, Agent, or Firm*—Weitzman Law Offices, LLC (57) ABSTRACT

An anti-pooling vest to be worn by a patient undergoing a hemodialysis procedure is disclosed for inhibiting intradialytic hypotensive symptoms in the patient during the course of hemodialysis treatment. The anti-pooling vest includes an inflatable bladder for applying a compressive pressure on the internal organs within the abdomen of the patient during the hemodialysis procedure to reduce the pooling of blood within the patient's internal organs. A pump, such as, for example, a manually compressible bulb or an electrically powered pump, in fluid communication with the bladder is operable to inflate the bladder to a predetermined pressure and a pressure relief valve in fluid communication with the bladder is operable to decrease the pressure within the bladder to the predetermined pressure. The anti-pooling vest may also be utilized to increase venous return in hypotensive patients in critical care suffering from blood or fluid loss by applying compressive pressure to the internal organs within the abdomen of the patient to reduce the pooling of blood within the patient's internal organs.

44 Claims, 9 Drawing Sheets

U.S. PATENT DOCUMENTS

| | | | |
|---|---|---|---|
| 4,928,674 A * | 5/1990 | Halperin et al. | 601/44 |
| 4,938,208 A | 7/1990 | Dye | |
| 5,222,478 A * | 6/1993 | Scarberry et al. | 601/44 |
| 5,346,472 A * | 9/1994 | Keshaviah et al. | 604/65 |
| 5,490,820 A * | 2/1996 | Schock et al. | 601/41 |
| 5,569,170 A * | 10/1996 | Hansen | 601/150 |
| 5,628,721 A * | 5/1997 | Arnold et al. | 602/19 |
| 5,853,396 A | 12/1998 | Bennes et al. | |
| 6,036,662 A * | 3/2000 | Van Brunt et al. | 601/41 |
| 6,114,303 A | 9/2000 | Blue et al. | |
| 6,485,427 B1 | 11/2002 | Lee et al. | |
| 6,615,077 B1 | 9/2003 | Zhu et al. | |
| 6,757,916 B2 | 7/2004 | Mah et al. | |
| 7,104,967 B2 * | 9/2006 | Rothman et al. | 601/41 |
| 7,183,255 B2 | 2/2007 | Landry et al. | |
| 7,244,225 B2 * | 7/2007 | Loeb et al. | 600/17 |
| 7,252,646 B2 * | 8/2007 | Bolam et al. | 601/152 |
| 7,537,575 B2 * | 5/2009 | Hansen et al. | 601/41 |
| 2004/0039324 A1 | 2/2004 | Gelfand et al. | |
| 2005/0165334 A1 | 7/2005 | Lurie | |

OTHER PUBLICATIONS

Hidetaka Tenaka et al., Treatment of orthostatic intolerance with inflatable abdominal band, The Lancet, vol. 349, p. 175 (Jan. 18, 1997).

J.-C. Denq et al., Efficacy of compression of different capacitance beds in the amelioration of orthostatic hypotension, Clinical Autonomic Research, vol. 7, pp. 321-326 (1997).

Jen-Shih Lee, 1998 Distinguished Lecture: Biomechanics of the Microcirculation, An Integrative and Therapeutic Perspective, Annals of Biomechanical Engineering, vol. 28, pp. 1-13 (2000).

Adrianus A. J. Smit et al., Use of lower abdominal compression to combat orthostatic hypotension in patients with autonomic dysfunction, Clin. Auton. Res., vol. 14, pp. 167-175 (2004).

N. Yamamoto et al., Treatment of post-dialytic orthostatic hypotension with an inflatable band in hemodialysis patients, Kidney International, vol. 70, pp. 1793-1800 (2006).

PCT International Search Report for Int'l Appln. No. PCT/US08/76456, dated Nov. 28, 2008.

PCT Written Opinion for Int'l Appln. No. PCT/US08/76456, dated Nov. 12, 2008.

A.C. Guyton, Textbook of Medical Physiology, pp. 325-327 (W.B. Saunders Co. 4th ed. 1971).

"The MAST Manual," David Clark Company, Inc. (publication date unknown).

William H. Bickell et al., "Randomized Trial of Pneumatic Antishock Garments in the Prehospital Management of Penetrating Abdominal Injuries," Annals of Emergency Medicine, 16:6 Jun. 1987, pp. 653-658.

* cited by examiner

ANTI-POOLING VEST FOR PATIENTS UNDERGOING HEMODIALYSIS AND IN CRITICAL CARE

CROSS-REFERENCE TO RELATED APPLICATION

This application claims the benefit of U.S. Provisional Patent Application No. 61/000,436, filed Oct. 26, 2007, the entire disclosure of which is incorporated by reference herein.

FIELD

This application relates generally to medical devices, and more particularly, to a method, system and apparatus for minimizing the pooling of blood within the internal abdominal organs of a patient suffering from renal failure during hemodialysis treatments or of a critical care patient to make fluid or blood infusion more effective in improving cardiac filling to enhance cardiovascular functions.

BACKGROUND

Patients suffering from renal failure of the kidneys are often treated using hemodialysis procedures to remove excess fluid and metabolic wastes (e.g., urea, creatinine, etc.) accumulated in body tissue and blood. During hemodialysis, a patient's blood is shunted from the body through a hemodialysis machine for diffusion and ultrafiltration before being returned to the patient's circulation system. Hemodialysis treatments are typically performed three or perhaps four times per week on a patient having chronic renal failure, with each session lasting between three to five hours.

Patients undergoing hemodialysis treatment are prone to suffer from hypotensive (low blood pressure) symptoms, such as headache, dizziness, muscle cramping and vomiting. Despite the many improvements made to modern hemodialysis procedures, intradialytic hypotension in hemodialysis patients continues to be a major source of concern for the well being of the patient. Many hemodialysis patients experience chronic hypotension, which is abnormal decrease in the patients' blood pressure. For some of these patients, the intradialytic hypotensive symptoms are so severe that they cannot tolerate the hemodialysis procedure and must instead resort to peritoneal dialysis or renal transplant. Indeed, repeated development of these hypotensive symptoms is a key factor leading to the high mortality rate of hemodialysis patients.

For many hemodialysis patients, it is believed that the intradialytic hypotensive symptoms result from the pooling of blood within the internal organs in the abdominal area or waist of the hemodialysis patient. Some have proposed use of an inflatable abdominal band to improve orthostatic hypotension, which is associated with a decrease in systolic blood pressure when patients change from supine to standing position. For instance, N. Yamamoto et al., Treatment of post-dialytic orthostatic hypotension with an inflatable abdominal band in hemodialysis patients, KIDNEY INTERNATIONAL, 70:1793-1800 (Sep. 27, 2006), discloses use of an inflatable abdominal band to treat patients, who after their hemodialysis treatment, are suffering from post-dialytic orthostatic hypotension. H. Tanaka et al., Treatment of orthostatic intolerance with inflatable abdominal band, THE LANCET, 349:175 (Jan. 18, 1997), discloses use of an inflatable abdominal band to treat orthostatic hypotension in patients with orthostatic intolerance. A. Smit et al., Use of lower abdominal compression to combat orthostatic hypotension in patients with autonomic dysfunction, CLIN AUTON RES 14:167-175 (2004), discloses use of an elastic abdominal binding to increase standing blood pressure in patients with neurogenic orthostatic hypotension. J. Denq et al., Efficacy of compression of different capacitance beds in the amelioration of orthostatic hypotension, CLINICAL AUTONOMIC RESEARCH 7, 321-326 (1997), discloses use of compression garments such as an antigravity suit (G suit) in treating patients with chronic symptomatic orthostatic hypotension.

Other types of compressive devices are known in the art. For instance, U.S. Pat. No. 4,925,133 entitled "Hydraulic Buoyancy Force Suit" discloses a buoyancy force suit to reduce pooling of blood with the goal of maintaining consciousness of flying pilots. U.S. Pat. No. 4,534,338 entitled "Servo Operated Anti-G Suit Pressurization System" discloses a servo operated system for quickly pressurizing an aircraft pilot's anti-G suit during high energy maneuvers. U.S. Pat. No. 4,938,208 entitled "Full Length Compressible Sleeve" discloses a sleeve for applying compressive pressure against a patient's limb to prevent pooling of blood in a patient's limb. Similarly, arterial pressure sphygmomanometers include an inflatable compression band worn about a patient's arm to identify diastolic and systolic arterial pressure. Non-inflatable work wear or belts that wrap around a person's waist are used to reduce the load on the back by providing additional support for the spine.

None of these references, however, address treatment of intradialytic hypotension occurring during the hemodialysis treatment. It is, therefore, desirable to reduce the pooling of blood in the abdominal organs of the patient during hemodialysis treatments in order to eliminate the development of intradialytic hypotensive symptoms over the course of hemodialysis.

Patients in critical care may also encounter similar problems resulting from trauma or burns. Reducing the pooling of blood in the abdominal organs of such critical care patients can lead to more effective fluid and blood infusion and improve cardiac filling to enhance cardiovascular functions of these seriously ill patients. Therefore, it is also desirable to reduce the pooling of blood in the abdominal organs of critical care patients to make fluid or blood infusion more effective in improving cardiac filling to enhance cardiovascular functions.

SUMMARY

In one aspect of the disclosure, an anti-pooling vest to be worn by a patient undergoing a hemodialysis procedure is disclosed for inhibiting intradialytic hypotensive symptoms in the patient during the course of hemodialysis treatment. The anti-pooling vest including an inflatable bladder for applying a compressive pressure on the internal organs within the abdomen of the patient during the hemodialysis procedure to reduce the pooling of blood within the patient's internal organs. A pump in fluid communication with the bladder is operable to inflate the bladder to a predetermined pressure and a pressure relief valve in fluid communication with the bladder is operable to decrease the pressure within the bladder to the predetermined pressure.

In another aspect of the disclosure, a method is disclosed for inhibiting intradialytic hypotensive symptoms in a patient undergoing a hemodialysis procedure. The method comprises applying compressive pressure to the internal organs within the abdomen of the patient during the hemodialysis procedure to reduce the pooling of blood within the patient's internal organs. The method further comprises adjusting the compressive pressure to a predetermined pressure associated with a time elapsed during the hemodialysis procedure.

In another aspect of the disclosure, a system is disclosed for inhibiting intradialytic hypotensive symptoms in a patient undergoing a hemodialysis procedure. The system comprises an inflatable bladder worn by the patient for applying a compressive pressure on the internal organs within the abdomen of the patient during the hemodialysis procedure to reduce the pooling of blood within the patient's internal organs. A pump in fluid communication with the bladder is operable to inflate the bladder to a predetermined pressure corresponding to a desired pressure at a particular time during the hemodialysis procedure. A pressure relief valve in fluid communication with the bladder is operable to decrease the pressure within the bladder to the predetermined pressure. A pressure sensor measures the pressure within the inflatable bladder, wherein the pump is activated to increase the pressure within the bladder when the measured pressure is below the predetermined pressure, and the relief valve is activated to decrease the pressure in the bladder when the measured pressure is above the predetermined pressure.

In another aspect of the disclosure, a method is disclosed for increasing venous return in a hypotensive patient suffering from blood or fluid loss. The method comprises applying compressive pressure to the internal organs within the abdomen of the patient to reduce the pooling of blood within the patient's internal organs. The compressive pressure may be applied to the patient's internal organs by inflating a bladder worn by the patient about the patient's abdomen to a predetermined pressure.

These and other advantages of the present disclosure will be apparent to those of ordinary skill in the art by reference to the following detailed description and the accompanying drawings.

DETAILED DESCRIPTION

An anti-pooling wear or vest 10 is disclosed herein for preventing the pooling of blood in the organs within the abdomen or waist of a patient. The anti-pooling vest 10 may be used for a variety of medical purposes, including, but not limited to, countering the development of intradialytic hypotensive symptoms in patients undergoing hemodialysis and/or improving cardiac filling to enhance cardiovascular functions in critical care patients suffering from trauma or burns. This disclosure also includes methods and protocols to pressurize the patient's abdominal organs to one or more preset or predetermined pressures during and after the treatment, designs of the anti-pooling vest 10 to best-fit patient's abdominal contour, and safety features of the anti-pooling vest 10 for the patient's well being.

Anti-Pooling Vest with Manual Operation

Figure 1:
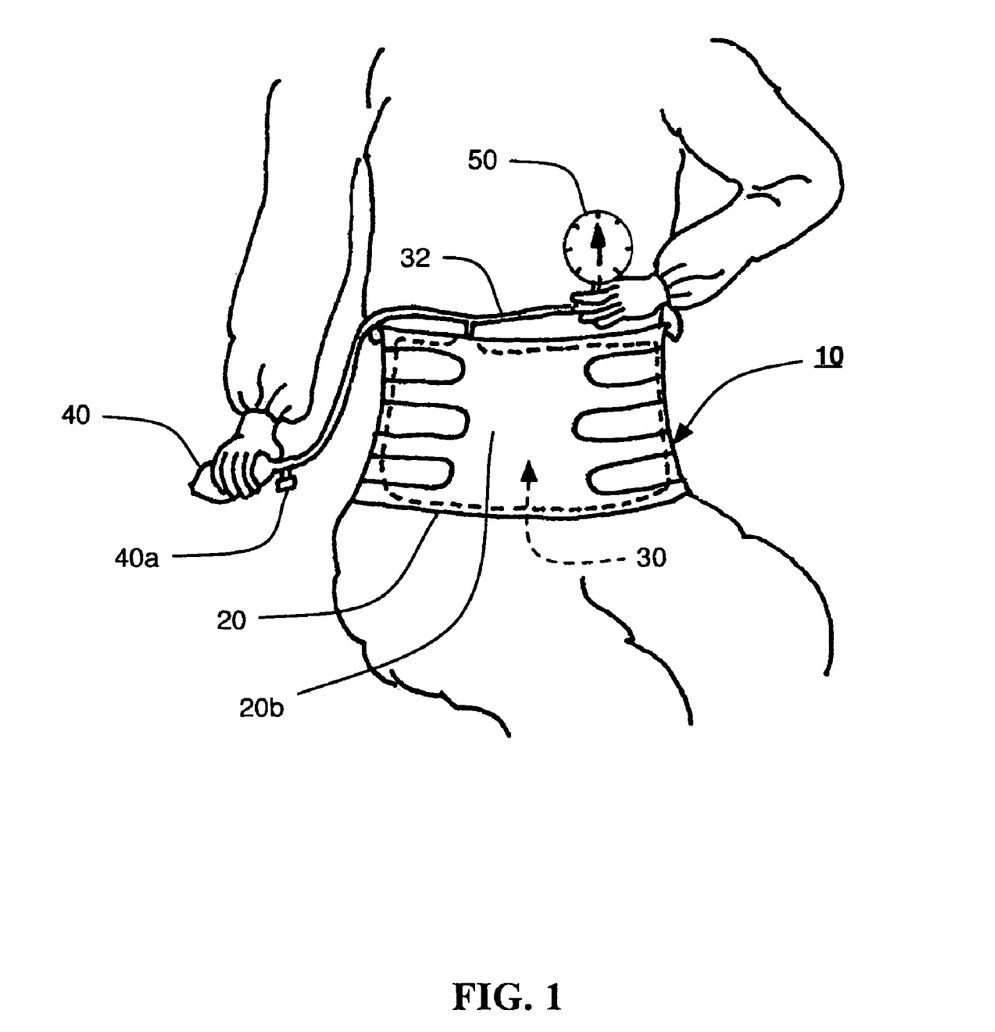
FIG. 1 illustrates a preferred anti-pooling vest worn around the waist of a patient in accordance with the present disclosure.

FIG. 1 illustrates a preferred anti-pooling wear or vest 10 worn around the waist or abdomen of a patient. The vest 10 includes a flexible band 20 and an inflatable bladder 30 with tubing 32 that may be pressurized using a manual pressurization system 40. An automatic pressurization system, such as the system described further below and illustrated in FIGS. 6-8, may be substituted for the manual pressurization system 40.

Figure 1A:
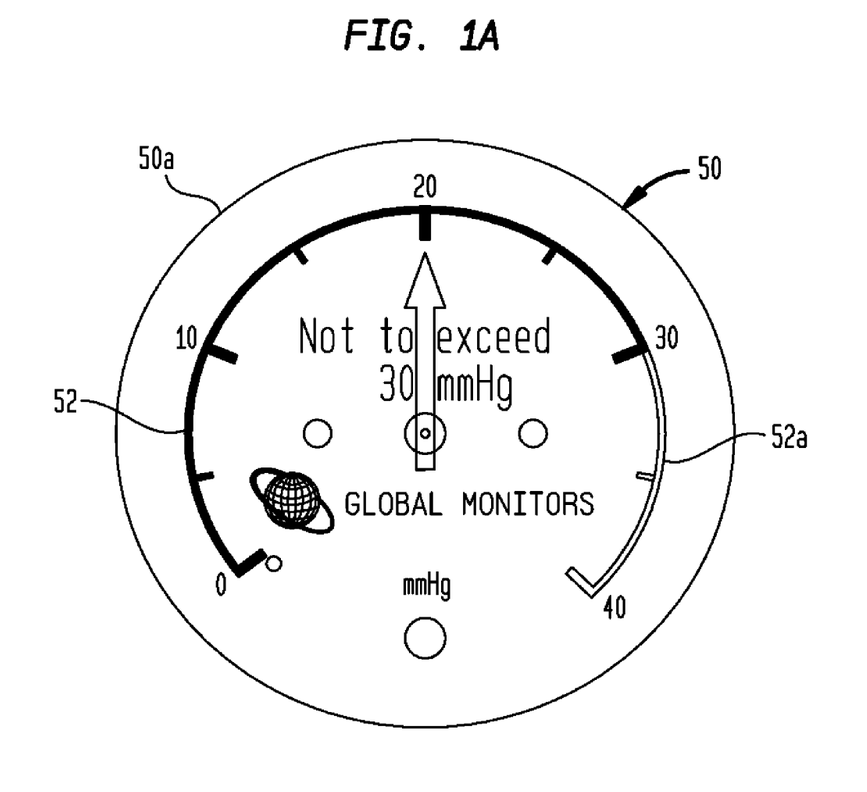
FIG. 1A illustrates the dial of a preferred pressure gauge utilized with the anti-pooling vest illustrated in FIG. 1.

A patient is illustrated in FIG. 1 squeezing a manual pump or bulb 40 to increase pressure in the inflatable bladder 30, which is located within the vest 10. The pressure within the inflatable bladder 30 is displayed on a pressure dial or gauge 50, which is shown in FIG. 1 as being held in the patient's other hand. A preferred dial 50a of the pressure gauge 50 is illustrated in FIG. 1A. The dial 50a preferably includes a plurality of markings indicative of pressure in, for example, mm Hg, with a region 52a of the markings being highlighted to indicate that pressure above a preset or predetermined maximum threshold (e.g., above 30 mm Hg) for use with the anti-pooling vest 10. To ensure proper use of the anti-pooling vest 10, instruction labels may be provided on the vest, as well as a nametag for the patient and/or health care professional to write the patient's name.

Figure 2:
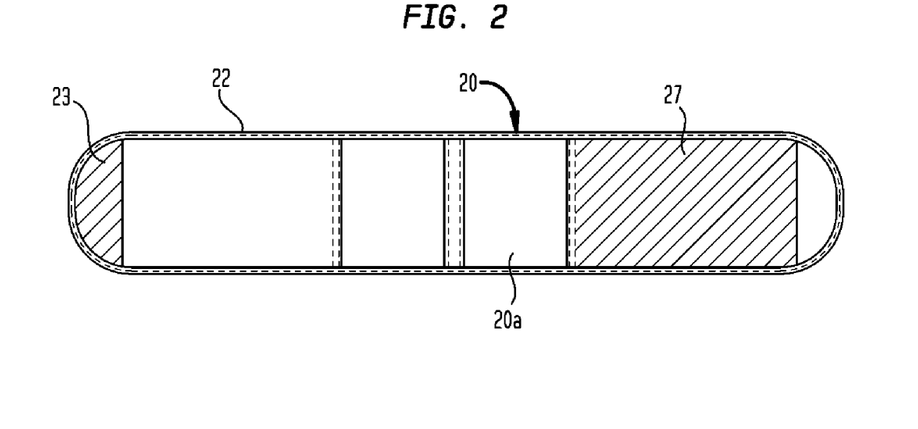
FIG. 2 is a plan view of the inner surface of a preferred embodiment of the anti-pooling vest illustrated in FIG. 1.
Figure 2A:
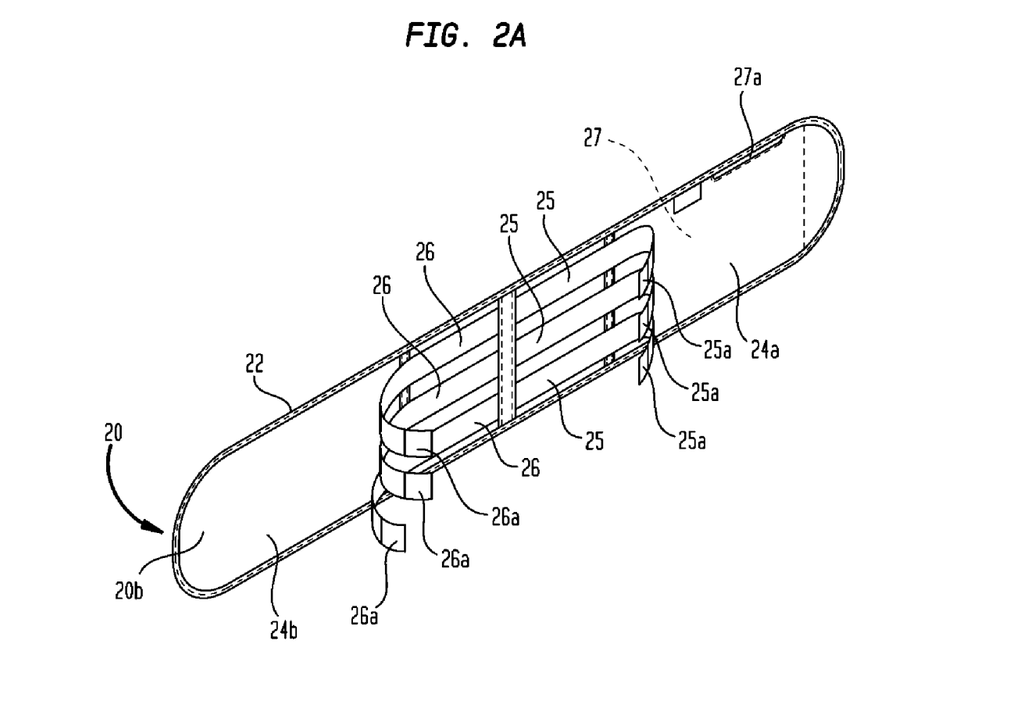
FIG. 2A is a perspective view illustrating the outer surface of the anti-pooling vest shown in FIG. 2.

A preferred embodiment of the band 20 is illustrated in FIGS. 2 and 2A. The band 20 is flexible so that it can be wrapped about the abdomen or waist of the patient. The band 20 is preferably made of nylon, such as, for example, polyurethane coated 420d Nylon fabric (420D/PU2 Nylon). Alternatively, the band 20 may be made from other suitable non-stretchable fabrics. The band 20 may be, for example, approximately eight to ten inches wide and approximately 55 inches in length. The size of the band, its material and its color may be modified to fit the need or preference of the patient.

The inner or back surface 20a of the band 20 is illustrated in FIG. 2. This is the surface 20a that contacts the patient when the band 20 is wrapped about the abdomen or waist of the patient as illustrated in FIG. 1. A webbing trim 22, such as, for example, a ⅞ inch polypropylene (PP) webbing trim, may be provided around the edges of the band 20. The inner surface 20a of the band 20 preferably includes an area 23 provided with a plurality of fasteners, such as Velcro® brand hook fasteners, for releasably engaging corresponding fasteners, such as Velcro® brand loops 24a, 24b, located on the front surface 20b of the band 20.

The front or outer surface 20b of the band 20 is illustrated in FIG. 2A. The outer surface 20b is the surface of the band 20 that is exposed when the band is wrapped about the abdomen or waist of a patient as illustrated in FIG. 1. The outer surface 20b preferably includes an area 24a, 24b containing a plurality of fasteners, such as Velcro® brand loops. When the band 20 is wrapped about the abdomen or waist of a patient with the inner surface 20a in contact with the patient as is shown in FIG. 1, the band may be releasably held in place by bringing the area 23 containing the plurality of hook fasteners into contact with the corresponding loops in the area 24a on the outer surface 20b of the band. It is understood that the arrangement of hook and loop fasteners may be reversed so that the loop fasteners are arranged in area 23 and the hook fasteners in area 24a, 24b.

The band 20 also preferably includes one or more elastic bands or strips 25, 26, each strip having one end that is sewn or otherwise affixed to the outer surface 20b of the band 20 and an opposing end that is free from the outer surface. A fastener 25a, 26a, such as Velcro® brand hooks, is preferably connected to the free end of each of the elastic strips 25, 26. Each elastic strip 25, 26 is preferably two inches wide. In the embodiment illustrated in FIGS. 2 and 2A, the band 20 includes three spaced apart, elastic strips 25 having their free end with the fastener 25a extending in the direction of area 24a and three spaced apart, elastic strips 26 having their free end with the fastener 26a extending in the direction of area 24b. The preferred use of three pairs of elastic strips 25, 26 makes the band 20 more closely conform to the body contour of the patient for more effective compression of internal organs and provides a greater safety margin for the patient not to be overly compressed. It is understood, however, that the use of three pairs of elastic strips 25, 26 is exemplary and that the band may incorporate a greater number or lesser number of elastic strips 25, 26 than illustrated in the drawings.

As discussed above, the band 20 is first wrapped about the abdomen or waist of a patient to enclose most of the patient's internal organs. The band 20 is releasably held in place by bringing the area 23 containing the plurality of hook fasteners into contact with the corresponding loops in the area 24a on the outer surface 20b of the band. To better conform the band 20 to the contour of the patient's waist, the free end of each elastic strip 25 is stretched in the direction of area 24a and the free end of each elastic strip 26 is stretched in the direction of area 24b. When sufficient tension is placed on each strip to better conform the band 20 to the contour of patient's waist, then the elastic strips 25, 26 are releasably connected to the band by engaging the hook fasteners 25a, 26a on the free ends of the strips with the corresponding loop fasteners located in the areas 24a and 24b on the outer surface 20b of the band.

The band 20 also preferably includes a pouch or pocket 27 having an opening 27a through which the inflatable bladder 30 inserted for placement within the pocket 27. Alternatively, the inflatable bladder 30 may be an integral part or otherwise built into the band 20. In the preferred embodiment, the opening 27a is approximately five inches in length and the pocket 27 is approximately 19 inches in length to accommodate a 16 inch by seven inch inflatable bladder 30. The inside of the pocket 27 is preferably made from nylon, such as, for example, polyurethane coated 210d Nylon fabric (210D/PU2 Nylon). When the anti-pooling vest 10 is properly fitted on the patient and the inflatable bladder 30 in the pocket 27 is pressurized, the elastic straps 25, 26 and Velcro® brand hook and loop fasteners ensure uniform pressure compression of the patient's internal organs.

Figure 3:
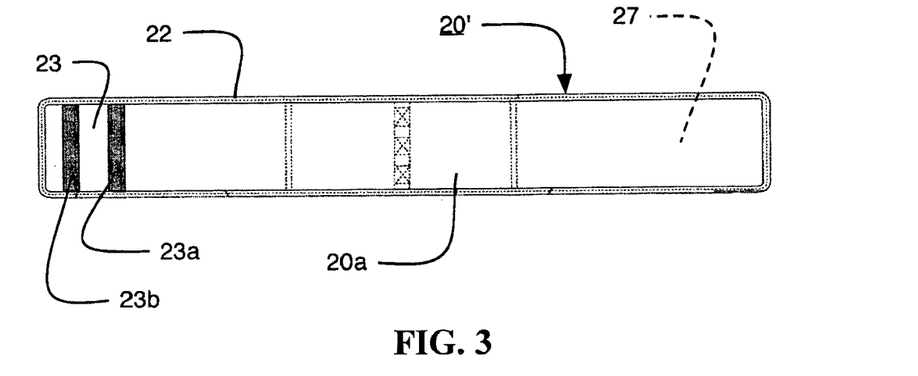
FIG. 3 is a plan view of the inner surface of another preferred embodiment of the anti-pooling vest.
Figure 3A:
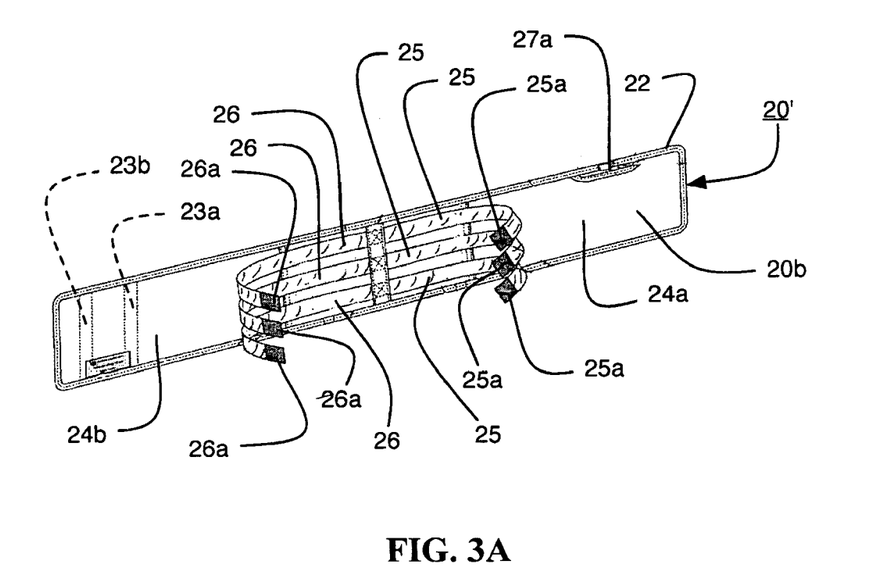
FIG. 3A is a perspective view illustrating the outer surface of the anti-pooling vest shown in FIG. 3.

Another preferred embodiment of the band 20' is illustrated in FIGS. 3 and 3A. The band 20' is similar to the band 20 illustrated in FIGS. 2 and 2A, with the exception that two strips 23a, 23b of fasteners, such as Velcro® brand hook fasteners, are provided in the area 23. These strips 23a, 23b may be affixed to the band 20' in a conventional manner, such as, for example, by sewing and/or using an adhesive. When the band 20' is wrapped about the abdomen or waist of a patient with the inner surface 20a in contact with the patient as is shown in FIG. 1, the band may be releasably held in place by bringing the two strips 23a, 23b of hook fasteners into contact with the corresponding loops in the area 24a on the outer surface 20b of the band. The construction and operation of the band 20' is similar to the band 20 described above in all other material respects.

Figure 4:
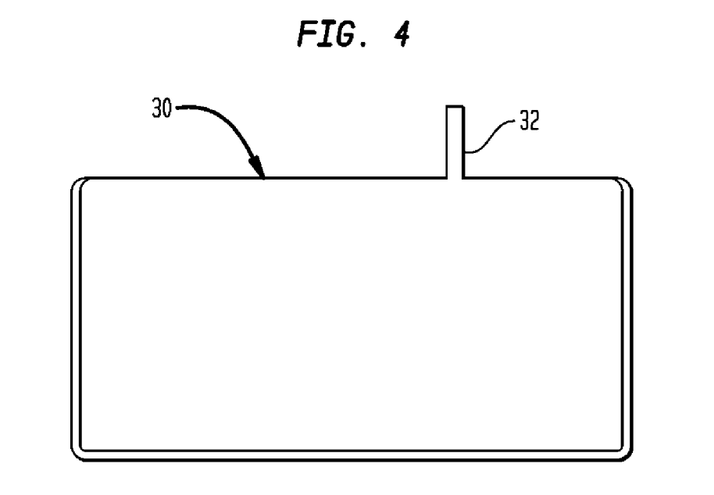
FIG. 4 illustrates a preferred inflatable bladder utilized with the anti-pooling vest illustrated in FIG. 1.

A preferred inflatable bladder 30 is illustrated in FIG. 4. The bladder 30 is preferably made of flexible polyvinyl chloride (PVC), rubber or other impermeable materials that can be inflated without air leakage. As discussed above, the bladder 30 is inserted through the opening 27a in the band 20, 20' to fit snugly to the pocket 27. Alternatively, the bladder 30 may be an integral part or otherwise built into the band 20. The bladder 30 may be, for example, a PVC sheet of 16 inches by fourteen folded to form a dimension of 16 inches by seven inches with three sides heat sealed. Other configurations of the bladder 30 may also be used with the anti-pooling vest 10. Hollow, flexible tubing 32 preferably extends from the bladder 30 to provide a fluid conduit to the pressurization system, pressure gauge and optional alarm.

Figure 4A:
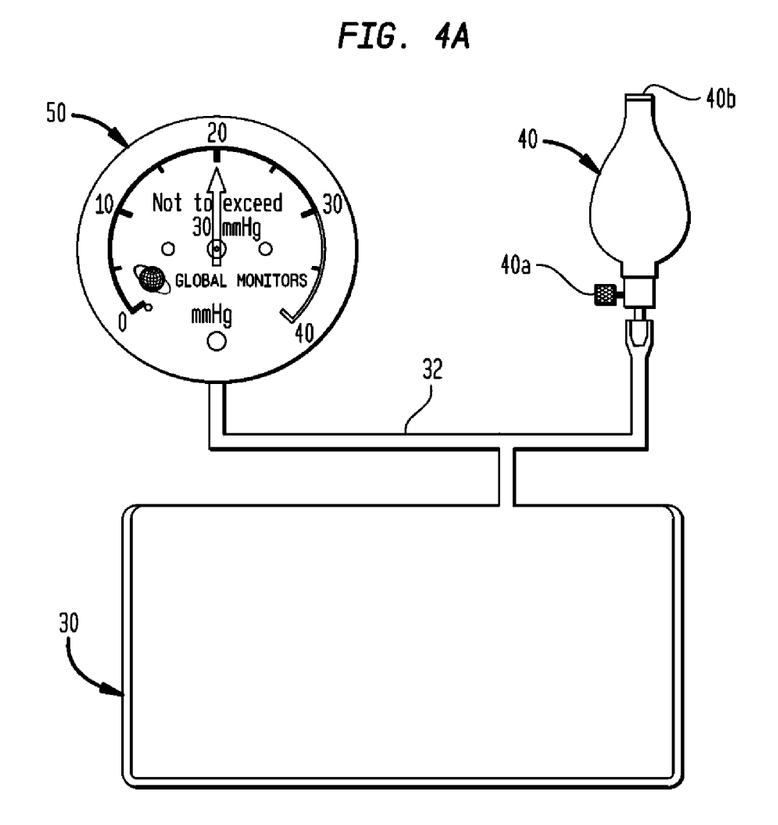
FIG. 4A illustrates the configuration of the inflatable bladder, tubing, manual pressurization system and pressure gauge utilized with the anti-pooling vest illustrated in FIG. 1.

FIG. 4A illustrates an exemplary configuration of the inflatable bladder 30, tubing 32, manual pressurization system 40 and pressure gauge 50 utilized with the anti-pooling vest 10. The manual pressurization system preferably includes a bulb or manual pump 40, a pressure release valve 40a, a pressure gauge 50, and an optional alarm (not shown). As is best illustrated in FIG. 1, the tubing 32 from the inflatable bladder 30 is preferably joined through a T-joint or other connector to the tubing 32 connected to the bulb 40 and pressure gauge 50. The functions of these components are described next.

When the pressure release control valve 40a of the bulb or manual pump 40 is set to the closed position, the repeated hand squeeze of the bulb by the patient or health care professional causes the bladder 30 to inflate to a predetermined, preset or desired pressure level as indicated by the pressure gauge 50. By turning the control valve 40a to the open position, the pressurized air in bladder 30 is released and the pressure in the bladder can return to zero. A one-way control valve 40b at the distal opening or air inlet of the bulb 40 only permits ambient air to enter the bulb 40 and flow from the bulb 40 as it is squeezed through the pressure release control valve 40a to inflate the bladder 30. When the bulb 30 is relaxed and returns to its normal configuration, air is allowed to flow through the one-way valve 40b from the atmosphere to fill up the bulb.

The pressure gauge 50 displays the pressure in the bladder 30, which corresponds to the pressure being imposed on the internal organs of the patient when the anti-pooling vest 10 is worn by the patient. A safety pressure release valve (not shown) may be incorporated into the pressure gauge 50 or elsewhere in the pressurization system to limit the maximum pressure that can be imposed by the anti-pooling vest 10 on the patient's waist and internal organs. Normally, the maximum pressure to inflate the bladder 30 would not exceed 20 mm Hg. Accordingly, the safety pressure release valve could be set to automatically open and release pressure in the bladder 30 that exceeds, for example, 30 mm Hg or 40 mm Hg.

An optional alarm may also be used with the anti-pooling vest 10 to make an audible sound at preset or predetermined time intervals to remind the health care professional and/or patient that it may be time to adjust the inflation pressure of the bladder 30 according to, for example, the preferred pressurization protocols described herein.

Manual Pressurization and Depressurization Protocol

Prior to starting the hemodialysis treatment, the anti-pooling vest 10 is placed about the abdomen or waist of the patient in the manner described above. Once the hemodialysis process is initiated with the patient, one course of pressurization of the inflatable bladder 30 will be a step increase of the pressure by about 3 to 5 mm Hg every half an hour of treatment.

Figure 5:
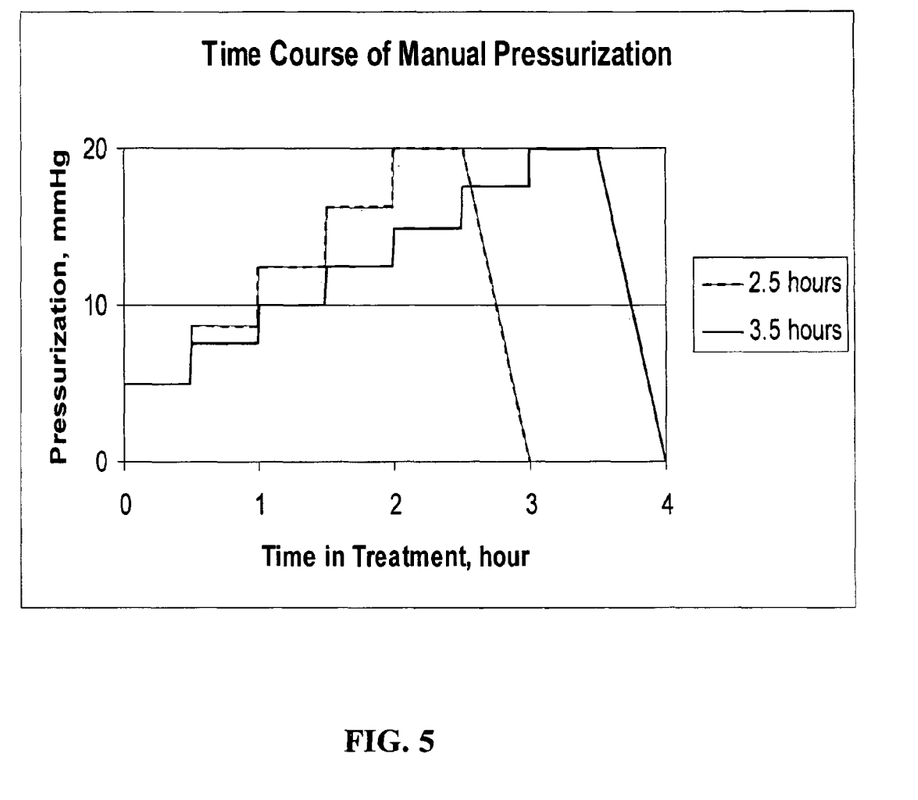
FIG. 5 is a graph illustrating the preferred manual pressurization of the anti-pooling vest over time during a hemodialysis treatment.

Two illustrative examples of preferred manual pressurization protocols are illustrated in FIG. 5. The first manual pressurization protocol illustrated in FIG. 5 is for a hemodialysis treatment period of approximately 2.5 hours. Prior to commencing hemodialysis treatment, the bladder 30 worn about the patient's abdomen or waist is preferably inflated to a predetermined or preset pressure of about 5 mm Hg by manually squeezing the bulb or pump 40 and the pressure is maintained at this level for about 30 minutes. The pressure in the bladder 30 is then increased to a second predetermined or preset pressure of about 9 mm Hg by manually squeezing the bulb or pump 40 and maintained at this level for about 30 minutes. After about an hour of treatment, the pressure in the bladder 30 is again increased to a third predetermined or preset pressure of about 12 mm Hg by manually squeezing the bulb or pump 40 and maintained at this level for another 30 minutes. After about 1.5 hours of treatment, the pressure in the bladder 30 is again increased to a fourth predetermined or preset pressure of about 16 mm Hg by manually squeezing the bulb or pump 40 and maintained at this level for 30 minutes. After about two hours of treatment, the pressure in the bladder 30 is increased to a fifth predetermined or preset pressure of about 20 mm Hg by manually squeezing the bulb or pump 40 and maintained at this pressure until the 2.5 hour treatment is completed. Once the 2.5 hour treatment period is completed, the patient preferably continues to wear the pressurized anti-pooling vest 10 for at least 30 minutes to an hour. During this time, the pressure in the bladder 30 is gradually reduced to zero using the pressure relief valve 40a to allow the blood volume in the patient's internal organs to gradually return to desirable levels without hypotension. Thereafter, the depressurized anti-pooling vest 10 may be removed from the patient.

The second manual pressurization protocol illustrated in FIG. 5 is for a hemodialysis treatment period of approximately three hours. Prior to commencing hemodialysis treatment, the bladder 30 worn about the patient's abdomen or waist is preferably inflated to a predetermined or preset pressure of about 5 mm Hg by manually squeezing the bulb or pump 40 and the pressure is maintained at this level for about 30 minutes. The pressure in the bladder 30 is then increased to a second predetermined or preset pressure of about 7.5 mm Hg by manually squeezing the bulb or pump 40 and maintained at this level for about 30 minutes. After about an hour of treatment, the pressure in the bladder 30 is again increased to a third predetermined or preset pressure of about 10 mm Hg by manually squeezing the bulb or pump 40 and maintained at this level for another 30 minutes. After about 1.5 hours of treatment, the pressure in the bladder 30 is again increased a fourth predetermined or preset pressure of to about 12.5 mm Hg by manually squeezing the bulb or pump 40 and maintained at this level for 30 minutes. After about two hours of treatment, the pressure in the bladder 30 is increased to a fifth predetermined or preset pressure of about 15 mm Hg by manually squeezing the bulb or pump 40 and maintained at this pressure for 30 minutes. After about 2.5 hours of treatment, the pressure in the bladder 30 is again increased to a sixth predetermined or preset pressure of about 17.5 mm Hg by manually squeezing the bulb or pump 40 and maintained at this level for 30 minutes. After about three hours of treatment, the pressure in the bladder 30 is increased to a seventh predetermined or preset pressure of about 20 mm Hg by manually squeezing the bulb or pump 40 and maintained at this pressure until the 3.5 hour treatment is completed. Once the 3.5 hour treatment period is completed, the patient preferably continues to wear the pressurized anti-pooling vest 10 for at least 30 minutes to an hour. During this time, the pressure in the bladder 30 is gradually reduced to zero using the pressure relief valve 40a to allow the blood volume in the patient's internal organs to gradually return to desirable levels without hypotension. Thereafter, the depressurized anti-pooling vest 10 may be removed from the patient.

Anti-Pooling Vest with Automatic Operation

Figure 6:
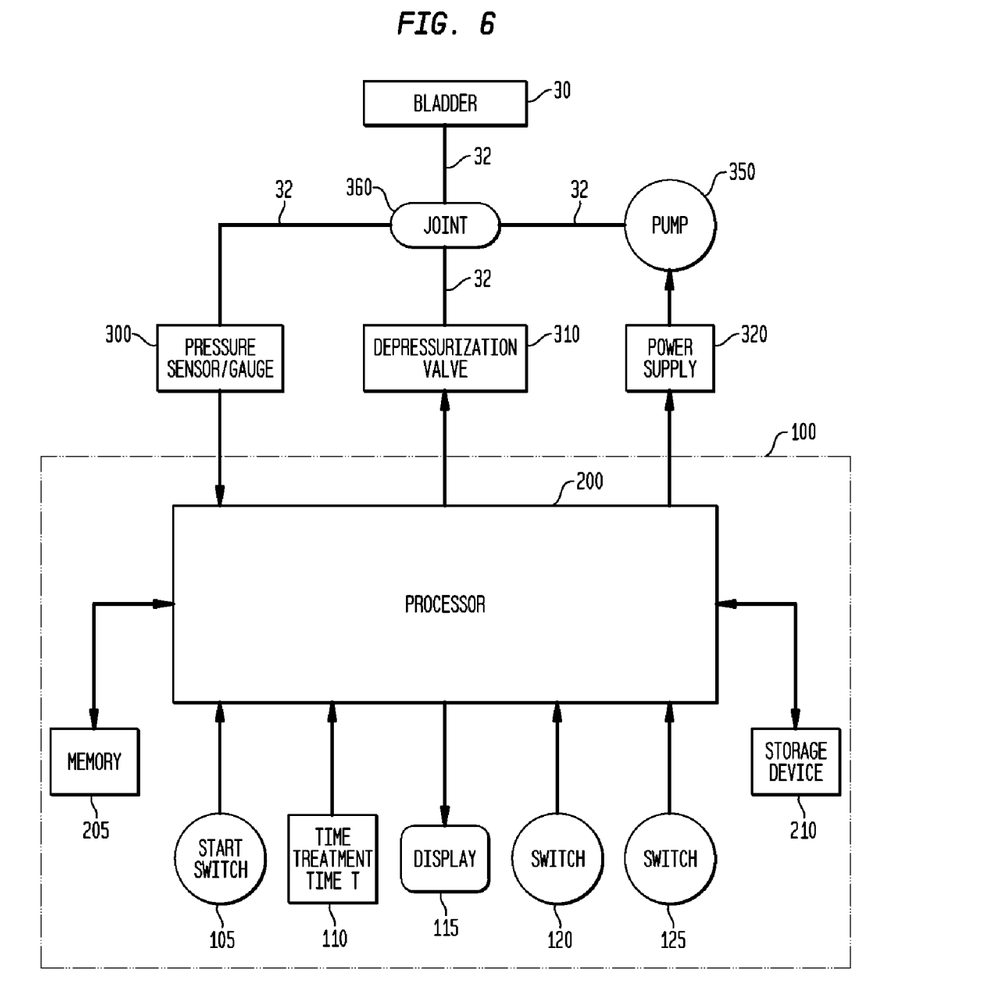
FIG. 6 is a schematic diagram of an automatic pressurization controller for pressurizing or depressurizing the inflatable bladder of the anti-pooling vest.

The anti-pooling vest may also be utilized with an automatic, programmable pressurization/depressurization system. A schematic diagram of a preferred automatic, programmable system for pressurizing or depressurizing the inflatable bladder 30 of the anti-pooling vest is illustrated in FIG. 6. The bladder 30 in the anti-pooling vest 10 may be inflated to predetermined, preset or desired pressures during and after the treatment in accordance with pressurization/depressurization protocols that correspond to the length of treatment and maximum desired pressure that have been selected by the physician and/or health care professional. The band 20, 20' and inflatable bladder 30 in the anti-pooling vest with automatic operation is identical in all material respects to that of the anti-pooling vest 10 described above with manual operation.

In the embodiment illustrated in FIG. 6, the inflatable bladder 30 in the anti-pooling vest worn about the patient's abdomen or waist is preferably connected by tubing or conduit 32 to an air pump 350, a depressurization valve 310, and a pressure sensor/gauge 300. A four way joint, pipe connector or other conventional fitting 360 may be utilized to facilitate fluid connection of the pump 350, depressurization valve 310, and pressure sensor/gauge 300. The pump 350 is preferably an electric pump that is powered by a pump power supply 320 and capable of generating sufficient air pressure to inflate the bladder 30 to the desired inflation pressure. When the pump 350 and depressurization valve 310 are not activated, no communication occurs between the joint 360 and atmosphere. For increased safety to ensure that the patient is not overly compressed by the automatic pressurization system, the pump 350 and its associated power supply 320 should preferably have the characteristic that the maximum deliverable pressure at zero flow is less than a preset or predetermined value.

The automatic pressurization/depressurization system also includes a controller 100 for controlling the pump 350 (and associated pressurization of the bladder 30) and the depressurization valve 310 to automatically achieve the desired pressurization/depressurization protocol, which will be discussed below with respect to FIG. 8. The controller 100 preferably includes a processor 200 (e.g., central processing unit ("CPU"), a memory 205 (e.g., random access memory ("RAM") and/or read only memory ("ROM")), and a storage device 210 (e.g., hard disk drive, compact disk drive, etc.). Various input/output devices are preferably connected to the processor 200, such as a display 115, start switch 105, timer 110, treatment period setting switch 120, maximum pressure setting switch 125, and pressure sensor/gauge 300.

Figure 7:
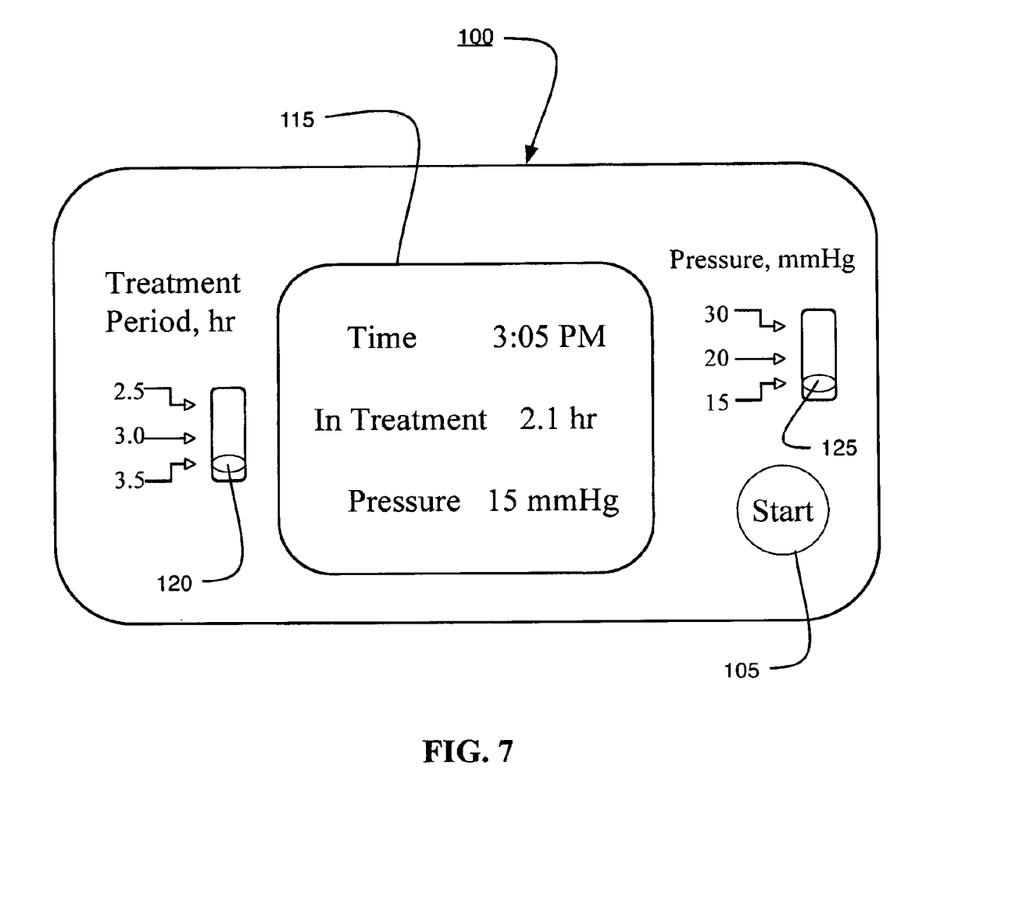
FIG. 7 illustrates a preferred display on an automatic pressurization controller for the anti-pooling vest.

A preferred display 115 on the automatic pressurization controller 100 for the anti-pooling vest is illustrated in FIG. 7. The controller 100 includes a start switch 105, treatment period setting switch 120, and maximum pressure setting switch 125. The physician or health care professional can activate the controller 100 and turn power on to all units in the controller by depressing the start switch 105.

Prior to starting the hemodialysis treatment using the automatic pressurization system, the anti-pooling vest 10 is placed about the abdomen or waist of the patient in the manner described above. The physician or other health care professional can select the treatment period for pressurization of the inflation bladder 30 by moving the selector switch 120 to the desired time interval (e.g., 2.5 hours, 3.0 hours, 3.5 hours, etc.). Similarly, the physician or other health care professional can select the maximum pressure to inflate the bladder 30 by moving the selector switch 125 to the desired maximum pressure (e.g., 15 mm Hg, 20 mm Hg, 30 mm Hg, etc.). It is understood that the number and value of the selector switch positions illustrated in FIG. 7 are exemplary and that this disclosure is not intended to be limited to the specific switch or a specific number of positions and/or values associated with those positions illustrated in the drawings.

The processor 200 is pre-programmed with a pressurization/depressurization protocol for each combination of time interval and maximum pressure settings of the switches 120, 125. Exemplary pressurization/depressurization protocols are discussed further below with respect to FIG. 8.

The display 115 preferably displays the current time, the time in treatment T, and the actual measured pressure P in the inflatable bladder 30 as measured by the pressure sensor/gauge 300. The timer 110 keeps the current time and records the time in treatment T, which information is communicated to the processor 200 and is also displayed on the display 115.

The processor 200 preferably derives the pressure P in the inflatable bladder 30 (without the oscillation associated with respiration) by averaging the pressure output from the pressure sensor/gauge 300. This ensures that pressure fluctuation due to the patient's breathing is removed. The pressure sensor/gauge 300 measures the actual pressure P in the inflatable bladder 30 and sends a signal associated with the measured pressure P to the processor 200 to determine when to activate the pump 350 and/or depressurization valve 310. The processor 200 executes the pre-programmed pressurization/depressurization protocol to adjust the pressure P in the inflatable bladder 30 based on the elapsed treatment time T input from the timer 110, the actual pressure P input from the pressure sensor/gauge 300, and the selected treatment period and maximum pressure settings from the switches 120, 125.

If the actual pressure P measured by the pressure sensor/gauge 300 is below the desired pressure, as determined by the pre-programmed pressure protocol, then the processor 200 activates the pump power supply 320 to drive the pump 350 to inflate the bladder 30. When the actual pressure P measured by the pressure sensor/gauge 300 reaches the desired pressure according to the pressure protocol, then the processor 200 deactivates the pump power supply 320 to turn the power off to the pump 350. As a safety feature, the voltage from the power supply 320 can be limited to not exceed a predetermined or preset voltage so that the pressure generated by the pump 350 cannot exceed a predetermined or preset pressure threshold, which is preferably a maximum pressure P of 30 mm Hg.

When the elapsed treatment time T measured by the timer 110 exceeds the preset treatment time according to the selected setting of the switch 120, the processor 200 activates the depressurization valve 310 by transmitting a signal to the solenoid on the depressurization valve to open the valve and slowly depressurize the inflatable bladder 30 by venting or otherwise releasing air from the bladder to atmosphere.

Figure 8:
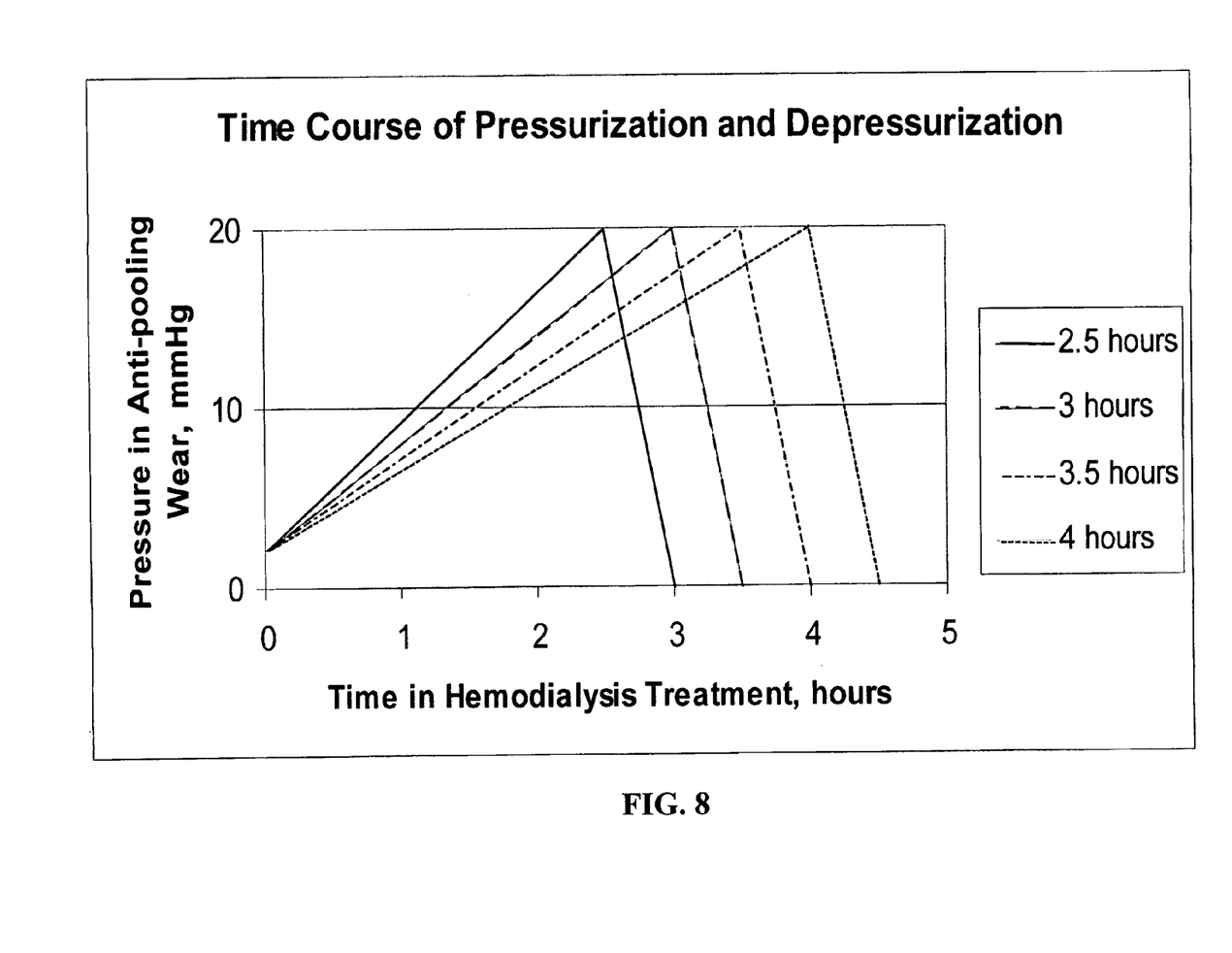
FIG. 8 is a graph illustrating the preferred pressurization of the anti-pooling over time by an automatic pressurization controller during a hemodialysis treatment.

Four exemplary automatic pressurization/depressurization protocols are illustrated in FIG. 8 to show the time course of the pressure to inflate the bladder 30 and thus to generate compression to the patient's abdominal organs. The four exemplary protocols are for a selected maximum pressure of 20 mm Hg for hemodialysis treatment times of 2.5 hours, three hours, 3.5 hours and four hours, respectively. The protocols illustrate a predetermined or preset increase in pressurization of the inflatable bladder 30 over time up to the maximum desired pressure and then the gradual decrease in pressure in the inflatable bladder for at least 30 minutes following the expiration of the hemodialysis treatment time. It is understood that the predetermined or preset inflation pressures correspond to the length of treatment and maximum desired pressure selected by the physician or other health care professional.

A higher compression pressure will reduce the blood volume in the patient's abdominal organs for the improvement of venous return, which will subsequently increase cardiac filling and cardiac output for the alleviation of hypotensive symptoms.

Because the improved venous return will lead to better cardiac filling and subsequently higher cardiac output, the improved cardiovascular functions may allow the physician to prescribe a higher rate of ultrafiltration for the patient during the course of hemodialysis. In this way, the hemodialysis treatment time may be reduced for the removal of the same volume of excess fluid that had been accumulated in the body tissue over the time between the previous hemodialysis treatment and the current one.

Once the patient completes the hemodialysis treatment, the patient would still wear the anti-pooling vest for the depressurization process. This process will allow the patient's cardiovascular system to adjust to the depressurization and to minimize the potential for blood to rapidly pool back to the abdominal organs and subsequently the development of hypotensive symptoms.

The physician could also prescribe the use of anti-pooling vest for home hemodialysis. Its use can shorten the time required to complete home hemodialysis and to reduce the incidence on the development of hypotensive symptoms.

Operation of the Anti-Pooling Vest for Patients with Trauma or Burns in Hospital's Critical Care Units Because of blood or fluid loss though trauma or burns, these patients are often hypotensive and require fluid or blood infusion. Some of the infused fluid or blood volume tends to expand the microcirculation and/or the macrocirculation. It is the latter that would determine the filling of the heart chambers. More cardiac filling would enable the non-damaged heart to increase cardiac output to deliver more blood flow to important organs. With better blood flow, the patient has a better and speedier chance for recovery. During the hypotensive stage, blood vessels may autoregulate for dilatation to allow more blood to flow through the vessel. The physician may prescribe the use of the anti-pooling vest to patients capable of accepting abdominal compression to counter the dilatation of blood vessels within the internal organs within the waist or abdomen of the patient for the improvement of venous return. As a result, the infused blood volume would become more effective to increase venous return, cardiac filling and subsequently cardiac output for the betterment of cardiovascular functions.

A low arterial pressure or low total blood volume is an indication of poor cardiovascular function. The larger the pressurization to be provided by the anti-pooling vest, the greater the shifting of blood from the internal organs toward the heart. Accordingly, the physician may select the level of pressurization to be inversely proportional to either the arterial blood pressure or the total blood volume of the patient.

The physician may order the use of appropriate medication, such as the use of vasoconstrictor eye drops or intramuscle injection, to further complement the anti-pooling function of the anti-pooling vest.

Having described and illustrated the principles of this application by reference to one or more preferred embodiments, it should be apparent that the preferred embodiment(s) may be modified in arrangement and detail without departing from the principles disclosed herein and that it is intended that the application be construed as including all such modifications and variations insofar as they come within the spirit and scope of the subject matter disclosed herein.

What is claimed is:

1. A method of inhibiting intradialytic hypotensive symptoms in a patient undergoing a hemodialysis procedure, comprising:
    elastically constraining the abdomen of the patient throughout the hemodialysis procedure while concurrently maintaining mobility of the patient's legs; and
    applying non-pulsating, gradually increasing compressive pressure to the internal organs within the abdomen of the patient according to a predefined protocol during the hemodialysis procedure, thereby reducing the pooling of blood within the patient's abdominal internal organs while concurrently allowing for unencumbered movement of the patient's legs during the hemodialysis procedure.

2. The method according to claim 1, wherein the protocol comprises adjusting the compressive pressure to a predetermined pressure associated with a time elapsed during the hemodialysis procedure.

3. The method according to claim 2, wherein the adjusting the compressive pressure comprises:
    adjusting the compressive pressure to a first predetermined pressure at the time when the hemodialysis procedure is initiated; and
    adjusting the compressive pressure to a second predetermined pressure after a predetermined time interval has elapsed during the hemodialysis procedure.

4. The method according to claim 3, wherein the second predetermined pressure is greater than the first predetermined pressure.

5. The method according to claim 4, further comprising adjusting the compressive pressure to a third predetermined pressure after a second predetermined time interval has elapsed during the hemodialysis procedure.

6. The method according to claim 5, wherein the third predetermined pressure is greater than the second predetermined pressure.

7. The method according to claim 6, wherein the third predetermined pressure is a maximum compressive pressure to be applied to the patient's abdominal internal organs.

8. The method according to claim 7, wherein the maximum compressive pressure does not exceed about 30 mm Hg.

9. The method according to claim 7, wherein the maximum compressive pressure does not exceed about 20 mm Hg.

10. The method according to claim 7, wherein the maximum compressive pressure does not exceed 15 mm Hg.

11. The method according to claim 3, further comprising gradually reducing the compressive pressure for a predetermined time interval after completion of the hemodialysis procedure.

12. The method according to claim 2, wherein the compressive pressure is applied to the patient's internal organs by inflating a bladder elastically constrained about the patient's abdomen.

13. The method according to claim 12, wherein the compressive pressure is adjusted by inflating the bladder with a manually operated pump.

14. The method according to claim 12, wherein the compressive pressure is adjusted by deflating the bladder.

15. The method according to claim 12, wherein the compressive pressure is automatically adjusted by a pump controlled by a controller.

16. The method according to claim 12, further wherein the protocol comprises:
    measuring the actual pressure within the bladder;
    activating the pump to increase the pressure within the bladder when the measured pressure is below the predetermined value; and
    activating a relief valve to decrease the pressure within the bladder when the measured pressure is above the predetermined value.

17. An anti-pooling vest to be worn by a patient undergoing a hemodialysis procedure of a specified duration in order to inhibit intradialytic hypotensive symptoms in the patient during the procedure, comprising:
    an elastic bladder support within the vest configured to constrain the abdomen of the patient, while concurrently allowing the patient unencumbered and unconstrained leg movement, for the duration of the hemodialysis procedure;
    an inflatable bladder supported by the bladder support that will apply a non-pulsating compressive pressure on the internal organs within the abdomen of the patient when the vest is worn during the hemodialysis procedure to thereby reduce the pooling of blood within the patient's internal abdominal organs;
    a pump in fluid communication with the bladder and operable to gradually inflate the bladder to a predetermined pressure during the hemodialysis procedure; and
    a pressure relief valve in fluid communication with the bladder through which pressure can be gradually released.

18. The anti-pooling vest according to claim 17, wherein the pump is a manually compressible bulb.

19. The anti-pooling vest according to claim 17, wherein the pump is electrically powered.

20. The anti-pooling vest according to claim 17, further comprising a pressure sensor for measuring the pressure within the bladder, wherein the pump is activated to increase the pressure within the bladder when the measured pressure is below the predetermined pressure, and the relief valve is activated to decrease the pressure in the bladder when the measured pressure is above the predetermined pressure.

21. The anti-pooling vest according to claim 20, wherein the predetermined pressure is based on the time elapsed during the hemodialysis procedure.

22. The anti-pooling vest according to claim 20, wherein the elastic bladder support comprises a flexible band having a proximal end, a distal end, an inner surface and an outer surface, the band including a pocket for receiving the inflatable bladder, wherein the band is adapted to wrap about the abdomen of the patient so that the bladder covers the patient's abdominal internal organs.

23. The anti-pooling vest according to claim 17, further comprising at least one fastener affixed to the proximal end of the band for releasably connecting to a corresponding fastener affixed to the distal end of the band when the band is wrapped about the abdomen of the patient.

24. The anti-pooling vest according to claim 23, wherein the at least one fastener is a Velcro-type fastener containing a plurality of hooks and the corresponding fastener is a Velcro-type fastener containing a plurality of loops.

25. The anti-pooling vest according to claim 23, further comprising an elastic strap having a first end and a second end, the first end affixed to the outer surface of the band and the second end having a fastener affixed thereto for releasably connecting to a corresponding fastener affixed to the outer surface of the band, wherein the second end of the strap may be stretched and releasably connected to the outer surface of the band to conform the band to the contour of the patient's abdomen after the band is wrapped about the abdomen of the patient.

26. The anti-pooling vest according to claim 25, wherein the fastener affixed to the second end of the elastic strip is a Velcro-type fastener containing a plurality of hooks and the corresponding fastener affixed to the outer surface of the band is a Velcro-type fastener containing a plurality of loops.

27. The anti-pooling vest according to claim 23, further comprising a plurality of elastic straps, each strap having a first end and a second end, the first end affixed to the outer surface of the band and the second end having a fastener affixed thereto for releasably connecting to a corresponding fastener affixed to the outer surface of the band, wherein the second end of each strap may be stretched and releasably connected to the outer surface of the band to conform the band to the contour of the patient's abdomen after the band is wrapped about the abdomen of the patient.

28. The anti-pooling vest according to claim 27, wherein the second end of at least one of the elastic straps extends and may be stretched in a direction toward the proximal end of the band, and the second end of at least one of the elastic straps extends and may be stretched in a direction toward the distal end of the band.

29. The anti-pooling vest according to claim 17, further comprising means for adjusting the pressure within the bladder to the predetermined pressure.

30. The anti-pooling vest according to claim 29, wherein the predetermined pressure corresponds to a desired pressure at a particular time during the hemodialysis procedure.

31. The anti-pooling vest according to claim 30, wherein the pressure in the bladder is increased to a maximum desired pressure during the hemodialysis procedure and gradually reduced for a predetermined time following the completion of the hemodialysis procedure.

32. The anti-pooling vest according to claim 31, wherein the maximum desired pressure does not exceed 30 mm Hg.

33. The anti-pooling vest according to claim 31, wherein the maximum desired pressure does not exceed 20 mm Hg.

34. The anti-pooling vest according to claim 31, wherein the maximum desired pressure does not exceed 15 mm Hg.

35. The anti-pooling vest according to claim 31, further comprising:
means for selecting the length of the hemodialysis procedure; and
means for selecting the maximum desired pressure;
wherein the predetermined pressure at any given time during the procedure is determined based on the selected length of the hemodialysis procedure and the selected maximum desired pressure.

36. A system for inhibiting intradialytic hypotensive symptoms in a patient undergoing a hemodialysis procedure, comprising:

an inflatable bladder adapted to be worn by the patient which is configured so that it will constrain the abdomen of the patient when worn, without concurrently constraining the limbs of the patient, while applying a non-pulsating, gradually increasing compressive pressure on the internal organs within the abdomen of the patient according to a predefined time-pressure protocol during a substantial portion of the hemodialysis procedure to thereby reduce the pooling of blood within the patient's internal organs while the hemodialysis procedure is occurring;
a pump in fluid communication with the bladder and operable to inflate the bladder to a predetermined pressure corresponding to a desired pressure at a particular time during the hemodialysis procedure;
a pressure relief valve in fluid communication with the bladder and operable to assist with regulation of the pressure within the bladder to about the predetermined pressure; and
a pressure sensor for measuring the pressure within the inflatable bladder, wherein the pump is activated to increase the pressure within the bladder when the pressure measured using the pressure sensor is below the predetermined pressure, and the relief valve is activated to decrease the pressure in the bladder when the pressure measured using the pressure sensor is above the predetermined pressure.

37. The system according to claim 36, wherein the pump is a manually compressible bulb.

38. The system according to claim 36, wherein the pump is electrically powered.

39. The system according to claim 36, further comprising a processor executing commands stored in a memory device, the processor:
determining the predetermined pressure for a given time during the hemodialysis procedure based on a pressurization/depressurization protocol stored in the memory device;
comparing the predetermined pressure to the measured pressure;
activating the pump to increase the pressure within the bladder when the measured pressure is below the predetermined pressure; and
activating the relief valve to decrease the pressure in the bladder when the measured pressure is above the predetermined pressure.

40. The system according to claim 39, further comprising:
means for selecting a length of the hemodialysis procedure; and
means for selecting a maximum desired pressure to inflate the bladder;
wherein the pressurization/depressurization protocol corresponds to the selected length of the hemodialysis procedure and the selected maximum desired pressure.

41. The system according to claim 36, wherein the pressure in the bladder is increased to a maximum desired pressure during the hemodialysis procedure and gradually reduced for a predetermined time following the completion of the hemodialysis procedure.

42. The system according to claim 41, wherein the maximum desired pressure does not exceed 30 mm Hg.

43. The system according to claim 41, wherein the maximum desired pressure does not exceed 20 mm Hg.

44. The system according to claim 41, wherein the maximum desired pressure does not exceed 15 mm Hg.

* * * * *